United States Patent
Coates et al.

(10) Patent No.: US 12,275,927 B2
(45) Date of Patent: Apr. 15, 2025

(54) MICROBIAL CONTAMINATION CONTROL IN BIOPROCESSING

(71) Applicant: The Regents of the University of California, Oakland, CA (US)

(72) Inventors: John D. Coates, Berkeley, CA (US); Ouwei Wang, Berkeley, CA (US); Victor M. Reyes-Umana, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 424 days.

(21) Appl. No.: 17/737,170

(22) Filed: May 5, 2022

(65) Prior Publication Data
US 2022/0259544 A1   Aug. 18, 2022

Related U.S. Application Data

(63) Continuation of application No. PCT/US2020/059564, filed on Nov. 6, 2020.

(60) Provisional application No. 62/931,726, filed on Nov. 6, 2019.

(51) Int. Cl.
| | | |
|---|---|---|
| *C12N 1/20* | (2006.01) | |
| *C12M 1/12* | (2006.01) | |
| *C12N 9/02* | (2006.01) | |

(52) U.S. Cl.
CPC ............... *C12M 37/00* (2013.01); *C12N 1/20* (2013.01); *C12N 9/0069* (2013.01); *C12Y 113/11049* (2013.01)

(58) Field of Classification Search
None
See application file for complete search history.

(56) References Cited

U.S. PATENT DOCUMENTS

| | | | | |
|---|---|---|---|---|
| 5,268,285 A | * | 12/1993 | Rogers ................. | A21D 8/047 435/320.1 |
| 2017/0029788 A1 | * | 2/2017 | Coates ................. | C12N 13/00 |
| 2017/0283685 A1 | * | 10/2017 | Coates ................. | C09K 8/528 |
| 2018/0298359 A1 | * | 10/2018 | Lee ....................... | C07K 16/18 |

OTHER PUBLICATIONS

Bender et al. "Sequencing and Transcriptional Analysis of the Chlorite Dismutase Gene of Dechloromonas agitata and Its Use as a Metabolic Probe". Applied and Environmental Microbiology, Oct. 2002, vol. 68, No. 10, pp. 4820-4826.*

Clark et al. "Structure and Evolution of Chlorate Reduction Composite Transposons". mBio, Aug. 2013, vol. 4, Issue 4, e00379-13, pp. 1-11.*

Hofbauer et al. "Structure and heme-binding properties of HemO (chlorite dismutase-like protein) from Listeria monocytogenes," Archives of Biochemistry and Biophysics, May 2015, vol. 574, pp. 36-48.*

International Search Report for priority PCT/US2020/059564, 9 pages (Feb. 9, 2021).

* cited by examiner

*Primary Examiner* — Vera Afremova
(74) *Attorney, Agent, or Firm* — Richard Aron Osman

(57) ABSTRACT

Biomanufacturing hygiene control in batch and fed-batch bioreactors is provided using a bioreactor employing a chlorite/Cld system, wherein the bioreactor comprises an engineered cultured cell expressing a recombinant cytoplasmic chlorite dismutase (cCld) sufficient to increase chlorite resistance of the cell, and chlorite sufficient to substantially inhibit growth of one or more contaminating microorganisms in the bioreactor yet not substantially inhibit growth of the cell.

9 Claims, 12 Drawing Sheets

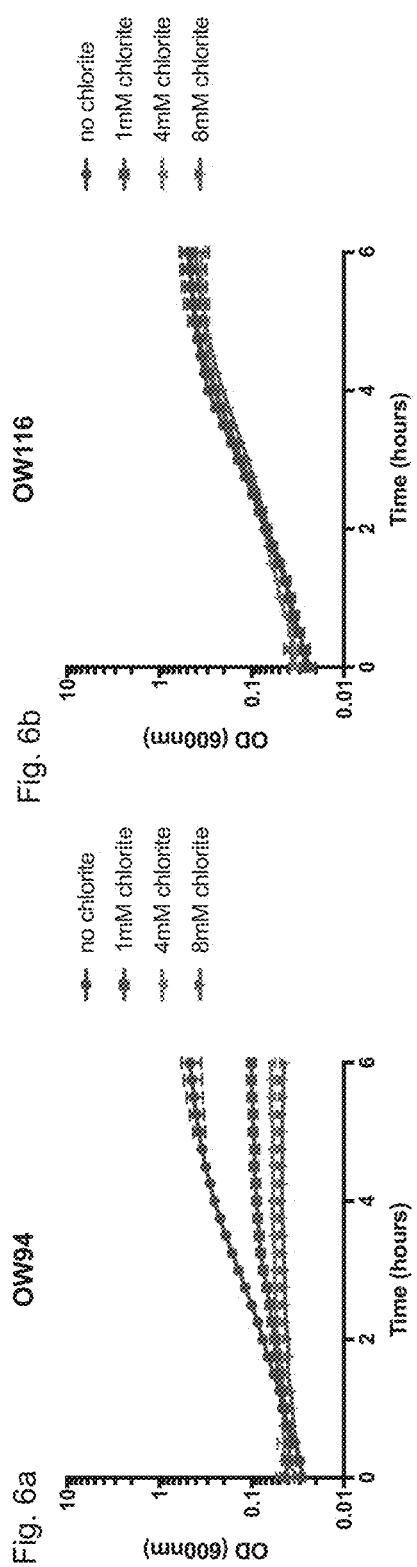
Fig. 6a
Fig. 6c
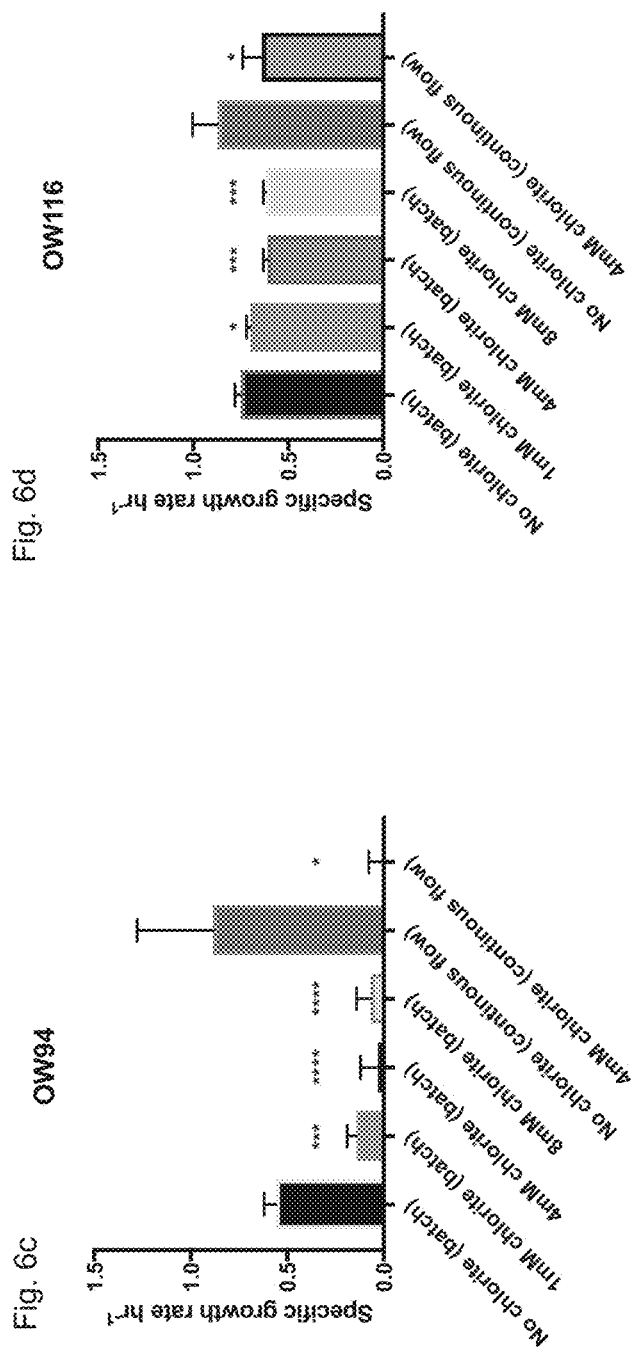
Fig. 6b
Fig. 6d

Figure 4:
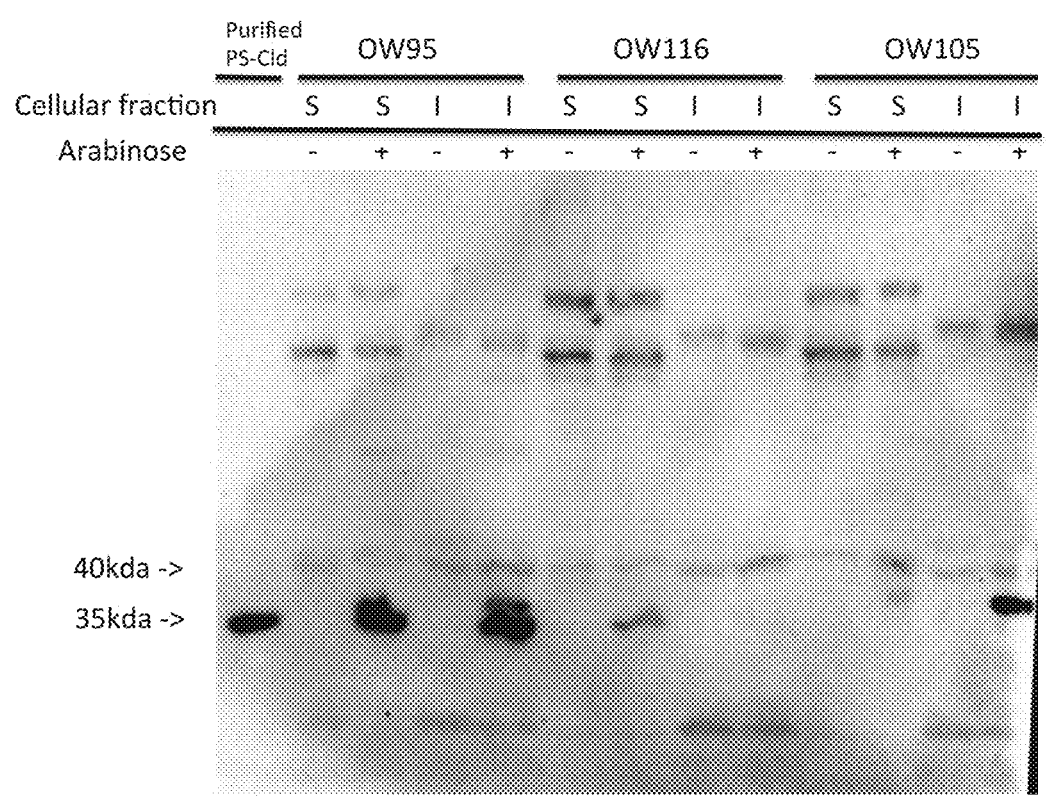
Figure 5A:
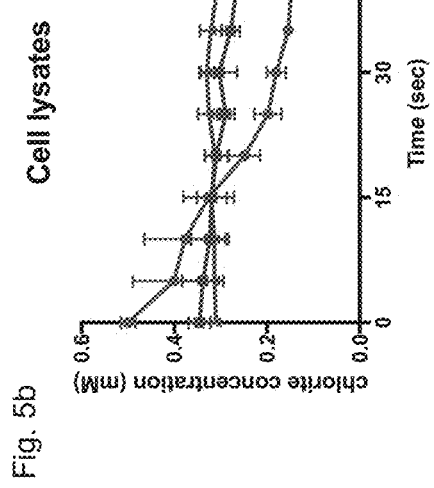
Figure 5B:
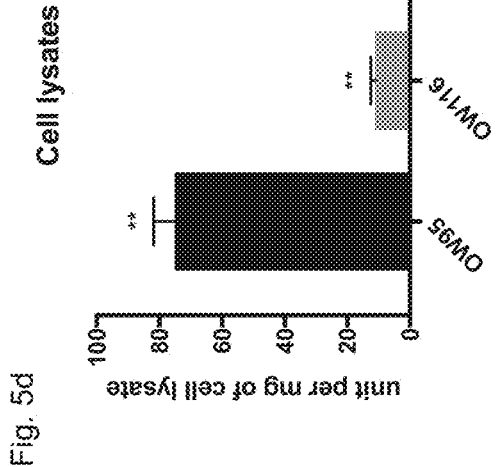
Figure 5C:
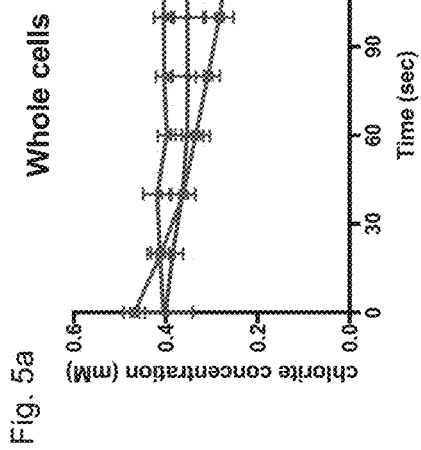
Figure 5D:
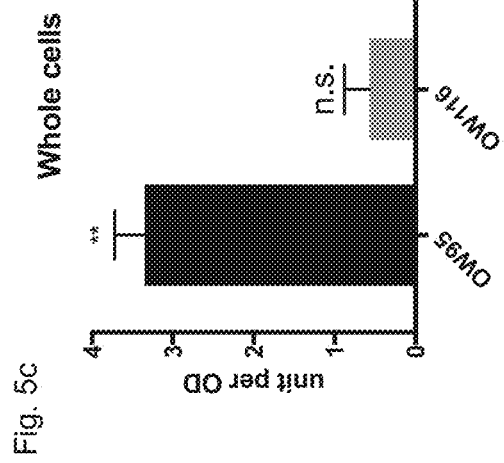
Figure 7A:
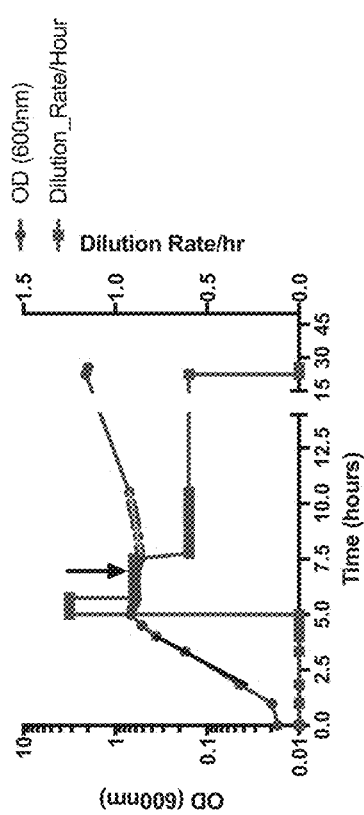
Figure 7B:
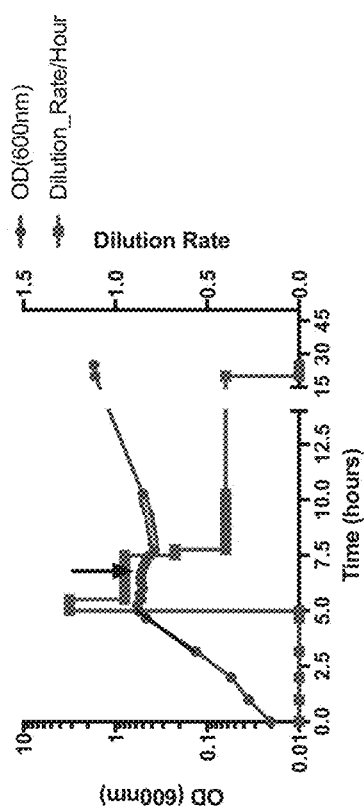
Figure 7C:
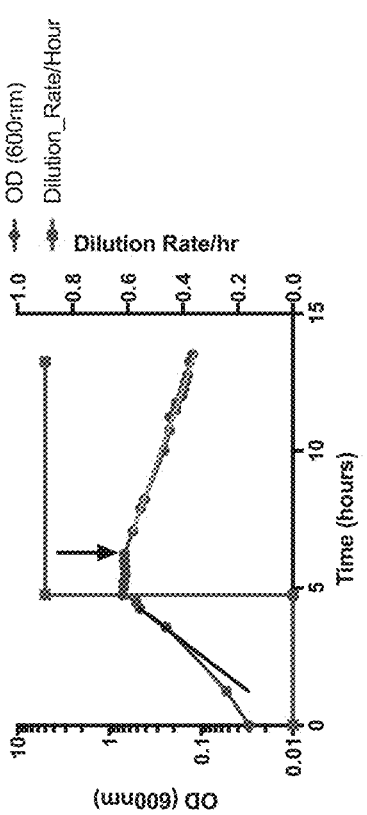
Figure 7D:
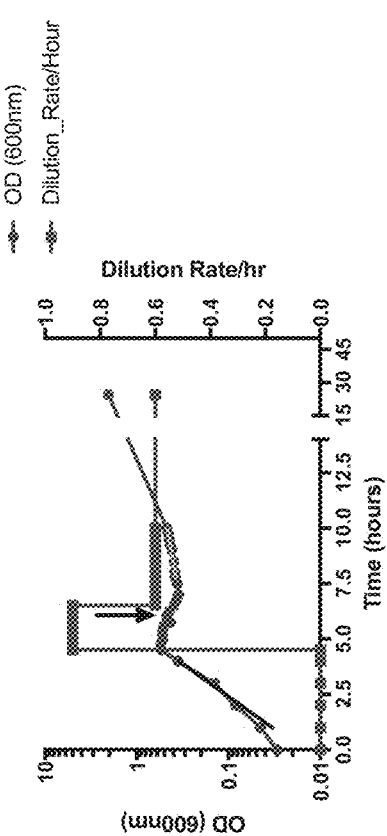
Figure 7E:
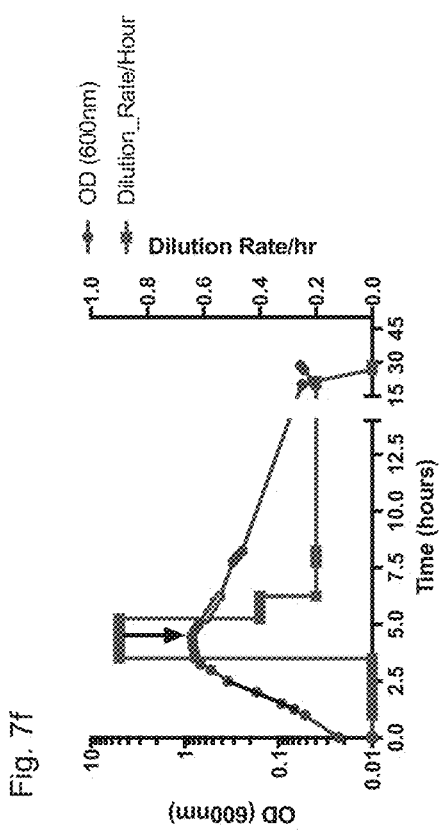
Figure 7F:
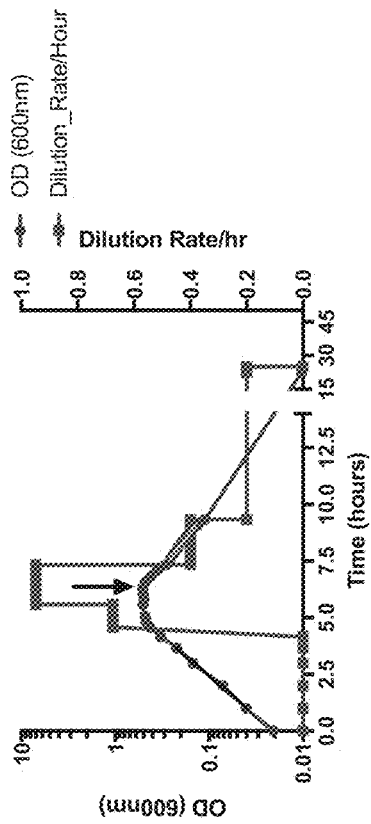
Figure 7G:
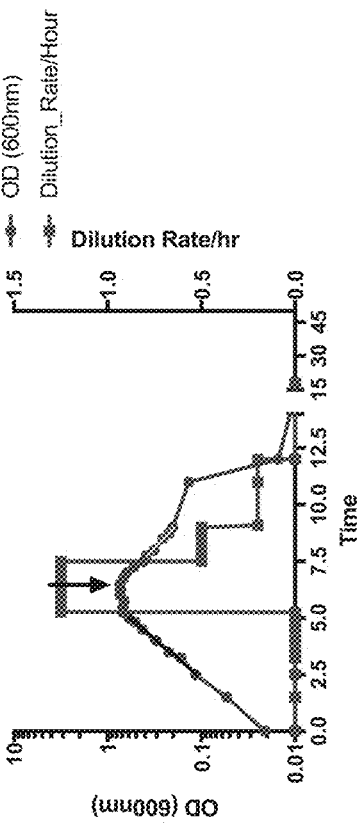

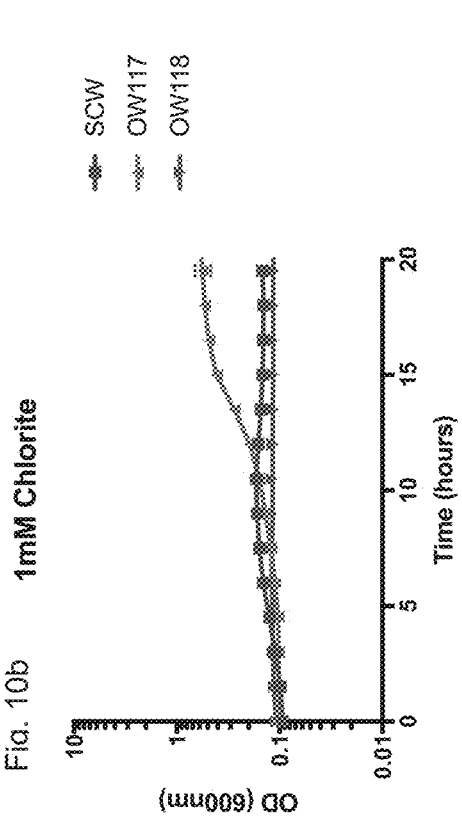
Fig. 10b 1mM Chlorite
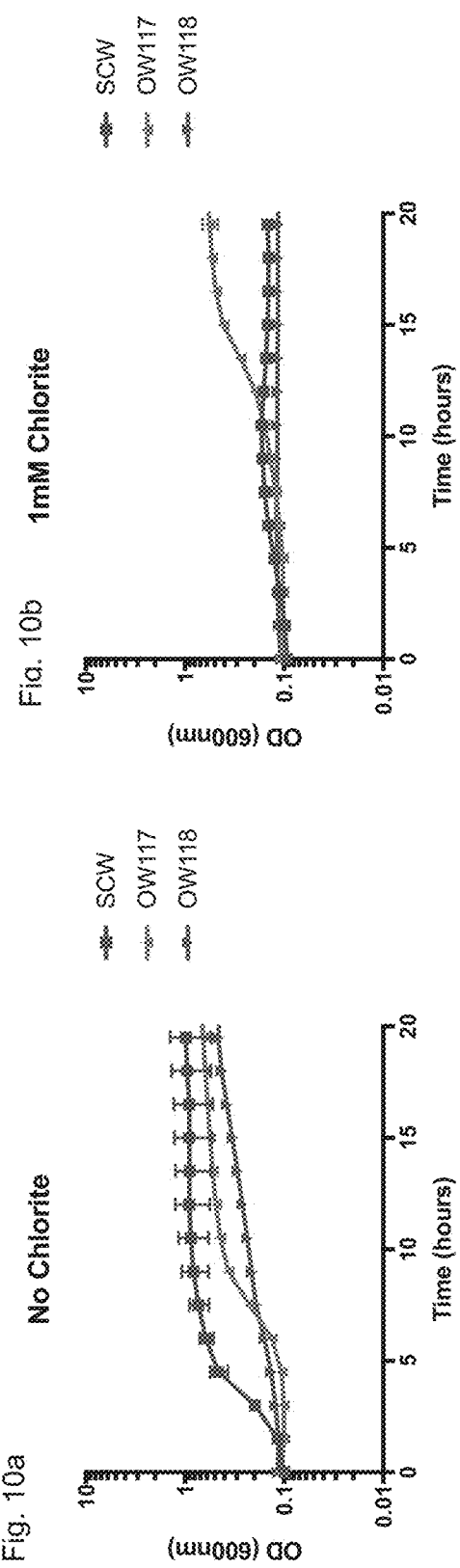
Fig. 10a No Chlorite
Fig. 10c 4mM Chlorite
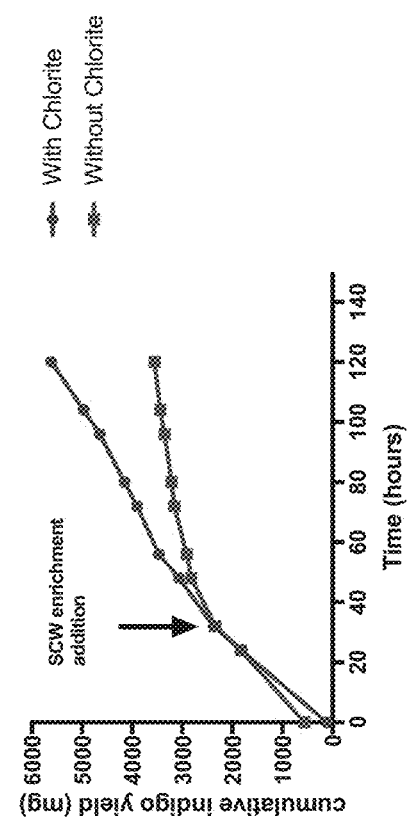
Fig. 10d
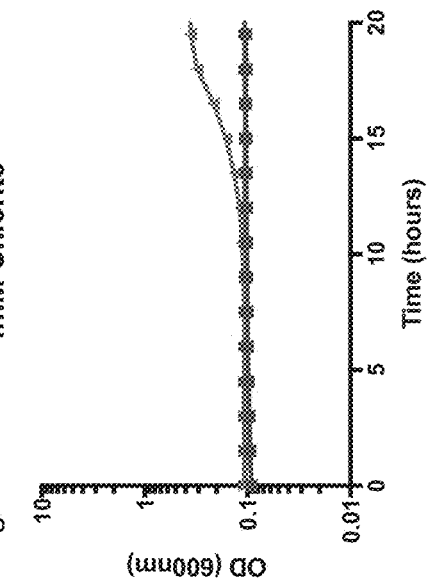

MICROBIAL CONTAMINATION CONTROL IN BIOPROCESSING

INTRODUCTION

The biotech industry often relies on bioreactors to develop and bio-transform value-added products from raw materials. In 2015, the biotech industry in the United States generated 107.7 billion U.S. dollars of revenue and had an estimated total market value of some 890 billion U.S. dollars. Most industrial scale bioprocessing bioreactors are operated as batch, fed-batch, and continuous-flow bioreactors. Batch reactors are simple, reliable and commonly used in the brewing and pharmaceutical industries, whereas fed-batch bioreactors are frequently implemented in processes that are subject to substrate inhibition. In theory, replacing the batch or fed-batch bioreactor system with a continuous-flow bioreactor would minimize equipment downtime, increase volumetric productivity, and reduce operational cost once the bioreactor reaches steady-state. However, due to the prolonged continuous operation, accidental bioreactor contamination with environmental microbes or bacterial phages is a major risk and subsequent failure investigation could cause factory shutdowns that disrupt production schedule. Failure data collected from an industrial fermentation plant during a 15-year period suggest 1 in 10 bioreactors are subjected to microbial contamination. Long-term continuous-flow bioreactor operation sometimes relies on antibiotic addition, which is ineffective against phage, environmentally unfriendly, and economically infeasible for low profit margin bio-commodity production.

We propose using chlorite as a biocide to solve the bioprocessing contamination problem. Chlorite ($ClO_2^-$) is a broad-spectrum alternative biocide that is known to be active against gram-negative and gram-positive bacteria [23-27, 29], bacteriophages [28], fungi [24], algae [26], and copepod parasites [30]. The chlorite toxicity is mediated by oxidation of cysteine and the thiol-containing antioxidant glutathione, resulting in detrimental cellular oxidative stress [23, 186]. The actual disinfection efficacy varies among these studies, presumably due to differences in microorganisms, chlorite concentrations, and media/buffer compositions.

The sodium chlorite salt is cheap, readily available, and relatively safe. Aside from being a disinfectant, recently published patents and scientific works established the use of acidified chlorite solution for meat and vegetable preservation. Commercially available immunomodulatory medicine, such as Oxoferin and WF10, contain chlorite as an active ingredient. Chlorite is exceptionally more cost-effective than traditional antibiotics, with one kilogram only costing about $1 when purchased directly from the manufacturer. Chlorite as a biocide should be compatible with current bioreactors as it has the lowest corrosion rate among chlorine-based disinfectants used in water distribution systems and residual chlorite can be readily removed via precipitation with reduced iron.

We hypothesized that the enzyme chlorite dismutase (Cld) could be used to confer chlorite tolerance or resistance in the bioprocessing host. Cld is a bacterial heme-containing, periplasmic enzyme that catalyzes the decomposition of chlorite to chloride ($Cl^-$) and molecular oxygen ($O_2$) [197-202]. It is highly conserved and essential in perchlorate and chlorate (collectively (per)chlorate) respiring bacteria that utilize (per)chlorate as their terminal electron acceptor [18, 19, 33, 148, 149, 203]. Heterologous expression of Cld in *Escherichia coli* has been reported numerous times [201, 204-211], but mostly with focus on purification and biochemical properties of the recombinant Cld. However, research has shown that wildtype chlorite dismutase (wtCld) is toxic to the production host, results in lower cell yield and poor growth kinetics. Furthermore, the wtCld does not confer chlorite resistance at temperatures above 26° C. As such, it is incompatible with many synthetic biology manufacturing processes. In addition, the wtCld's high specific activity toward chlorite reduce its usefulness as part of a contamination control technology. The added chlorite would be rapidly removed from the system reducing the biocidal efficiency of its addition and the inhibition of contaminating organisms.

SUMMARY OF THE INVENTION

The disclosed invention provides a non-naturally occurring, engineered cytoplasmic chlorite dismutase (cCld) enzyme to address above mentioned problems. The cCld lacks a functional N-terminal translocation peptide which results in an inability to translocate the active protein from the cell cytoplasm into the periplasm. By selectively protecting the cytoplasm—in contrast to wtCld which only protects the periplasm—the cCld confers hyper-chlorite resistance to biomanufacturing hosts. Unlike wtCld, cCld has minimal chlorite dismutase activity while conferring 5-fold higher chlorite resistance than wtCld. Our studies demonstrate that chlorite can be applied to rescue or revert a bioprocessing reactor back to the original axenic state, even after extensive outgrowth of a complex contaminating community.

In addition to providing robust hygiene control to a large-scale bioprocess, the chlorite/cCld technology can be applied in microbiology labs or production processes as a selection system to ensure the robust selection and maintenance of seminal genes within an recombinant host. Furthermore, this invention also enables the use of non-traditional feed stocks such as food or agricultural waste in bioreactors, which are normally deemed too dirty for bioprocessing due to increased risk in contamination.

As a particular embodiment we disclose construction of a chlorite hyper-resistant strain by functional expression of Cld (from *Shewanella algae* strain ACDC) in *E. coli*, followed by directed evolution. This strain exhibits a low Cld activity and is compatible with a continuous-flow bioreactor that contains chlorite as a biocide. We further show that chlorite can be applied in continuous-flow bioreactors to prevent contamination and rescue contaminated reactors back to a productive monoculture state.

The invention provides devices and methods to control for microbial contamination in commercial synthetic biology based biomanufacturing system. In an aspect the invention provides a bioreactor employing a chlorite/Cld system for hygiene control, the bioreactor comprising an engineered cultured cell expressing a recombinant cytoplasmic chlorite dismutase (cCld) sufficient to increase chlorite resistance of the cell, and chlorite sufficient to substantially inhibit growth of one or more contaminating microorganisms in the bioreactor yet permissive to, and not substantially inhibitory of, growth of the cell.

In embodiments:
the cCld comprises a mutation that inhibits signal peptide processing and/or translocation through the inner membrane, such as one or more point or deletion mutations within residues 2-31, such as a point mutation that is alanine to aspartate (A21D), or a deletion or truncation within the translocation signal peptide, the amendment of additional amino acid residue in the N-terminal of the Cld enzyme to block translocation, mutation after residue 31 in Cld enzyme that blocks translocation; all other mutations in Cld would result in a similar phenotype;

the cCld is heterologous to the cell (derived from a different species cell) and/or the cell does not endogenously express a chlorite dismutase;

the cell is cell is an animal cell, such as a mammalian or insect cell, a bacterial, yeast, or fungal cell. Exemplary bacterial, yeast, or fungal cells include without limitation the following species: *Saccharomyces* sp., *Saccharomyces cerevisiae, Saccharomyces monacensis, Saccharomyces bayanus, Saccharomyces pastorianus, Saccharomyces carlsbergensis, Saccharomyces pombe, Trichoderma reesei, Neurospora crassa, Neurospora* sp., *Kluyveromyces* sp., *Kluyveromyces marxiamus, Kluyveromyces lactis, Kluyveromyces fragilis, Pichia stipitis, Pichia pastoris, Pichia* sp., *Sporotrichum thermophile, Candida shehatae, Candida tropicalis, Neurospora crassa, Zymomonas mobilis, Clostridium* sp., *Clostridium saccharoperbutylacetonicum, Clostridium phytofermentans, Clostridium thermocellum, Clostridium beijerinckii, Clostridium acetobutylicum, Clostridium botulinum, Clostridium butyricum, Clostridium diolis, Clostridium ljungdahlii, Clostridium aerotolerans, Clostridium cellulolyticum, Clostridium tyrobutyricum, Clostridium pasteurianum, Moorella thermoacetica, Escherichia coli, Klebsiella oxytoca, Thermoanaerobacterium saccharolyticum, Yarrowia lipolytica, Yarrowia* sp., *Aspergillus* sp., *Fusarium venenatum, Fusarium oxysporum, Bacillus subtilis*, and *Bacillus* sp.

the one or more contaminating microorganisms are selected from the group consisting of prokaryotic microorganisms, bacteria, archaea, eukaryotic microorganisms, fungal cells, yeast, algae, and bacteriophages; such as bacteria is selected from the group consisting of *Lactobacillus, Clostridium, Pediococcus, Enterococcus, Acetobacter*, and *Gluconobacter;* the cultured cell produces an industrial fermentation product, such as a hydrocarbon or hydrocarbon derivative, such as ethanol, or butanol, or other products such as a fermentation based enzyme, specialty chemical, food ingredient, flavor and fragrances—the reactors and methods are amendable to producing essentially any fermentation based compound or product; and/or the bioreactor is a continuous flow bioreactor.

In an aspect the invention provides a method for microbial contamination control in bioprocessing and/or improving industrial fermentation hygiene, the method comprising operating a bioreactor as disclosed or claimed herein, with chlorite sufficient to substantially inhibit growth of one or more contaminating microorganisms in the bioreactor yet not substantially inhibit growth of the cell, such as wherein the chlorite is in an effective amount and/or concentration, and/or provided in an effective frequency and/or duration.

In an aspect the invention provides a method of culturing a cell, comprising: (a) culturing a cell recombinantly engineered to express a functional cytoplasmic chlorite dismutase (cCld) in a culture medium under conditions whereby the cCld is expressed in said cell, wherein said culture medium comprises one or more contaminating microorganisms, wherein the cCld is expressed in the cell; and (b) treating said culture medium with chlorite in an amount sufficient to kill said one or more contaminating microorganisms without killing said cell, wherein the cCld protects the cell from toxic effects of the chlorite.

The invention encompasses all combination of the particular embodiments recited herein, as if each combination had been laboriously recited.

BRIEF DESCRIPTION OF THE DRAWINGS

FIGS. 1*a*-1*c*: (a) Cld-expressing *Saccharomyces cerevisiae* and empty victor control growth with different chlorite concentrations. (b) *E. coli* and (c) *C. crescentus* phages deactivation by chlorite.

FIGS. 2*a*-2*b*: (a) Chlorite dose-response curves and (b) chlorite IC50 of different *E. coli* strains used in this study. Error bars represent the standard deviation of three biological replicates (n=3).

FIG. 3. Cld Western blot of wtCld expressing *E. coli* OW95, and cCld expressing *E. coli* OW116, and A21D mutant Cld expressing *E. coli* OW105. Letter S and I indicate soluble and insoluble cellular fractions of the input. + and − signs indicate whether arabinose was added for protein induction. Purified Cld was loaded as a positive control. The uncropped full western blot image can be find at FIG. 4.

FIG. 4. The uncropped full western blot image.

FIGS. 5*a*-5*d*: (a, b) Chlorite decomposition of whole cells and cell lysates of different strains overtime, respectively. (c, d) Cld activity of whole cells and cell lysates of different strains based on FIGS. 3*a* and 3*b*. One unit is defined as 1 μmol of chlorite decomposed by 1 OD/mL of cells or 1 mg of crude protein per minutes. ** indicates a p-value ≤0.01, n.s. indicates a P value >0.05. p-values are calculated based on T test vs. negative control OW94.

FIGS. 6*a*-6*d*: (a, b) Batch growth curves from RFP-expressing *E. coli* (OW94) and cCld-expressing *E. coli* (OW116) stationary cultures with different chlorite concentrations. (c, d) OW94 and OW116 specific growth rates of from batch culture stationary cells (batch) and continuous-flow bioreactor mid-log cells (continuous-flow). **, *, and * indicate a P value that ≤0.0001, ≤0.001, and ≤0.05, respectively. For batch cultures, p-values are calculated based on one-way ANOVA test vs. batch no chlorite controls. For continuous-flow cultures, p-values are calculated based on T test vs. continuous-flow no chlorite controls.

FIGS. 7*a*-7*g*. cCld expressing *E. coli* OW116 (a-d) and RFP expressing *E. coli* OW94 (e-g) bioreactors, showing changes in OD600 nm before and after chlorite spike. Dilution rate was adjusted to maintain a growth equilibrium state before and after chlorite addition. Black and green bars indicate ranges used for specific growth rate calculation. Black arrows indicate chlorite spiking.

FIG. 8. Differentially expressed stress-induced proteins in response to chlorite addition in OW94 and OW116. Fold change is calculated based on normalized peptides abundance. A protein with a confidence score >100, p-value <0.05, and maximal normalized peptide abundance fold change >2, is considered differentially expressed.

FIGS. 9*a*-9*e*. (a) Visual changes of RFP and cCld expressing OW115 bioreactor overtime, Strawberry Creek water was added along with OW115 inoculum at day 0 (not shown here), and chlorite was added at day 2 morning. (b-d) Flow cytometry quantification of total cells and RFP+ cells in three separated bioreactor runs. Black arrow indicates chlorite spiking. (e) Control reactor without chlorite that was contaminated.

FIGS. 10*a*-10*d*. (a-c) Batch growth curves of Strawberry Creek enrichment (SCW), cCld and Fmo expressing *E. coli*

(OW117), and Fmo expressing *E. coli* (OW118) with different chlorite concentrations. (d) Cumulative indigo yield in OW117 bioreactor, with or without chlorite. Contaminant was added after 30 hours.

Figure 11:
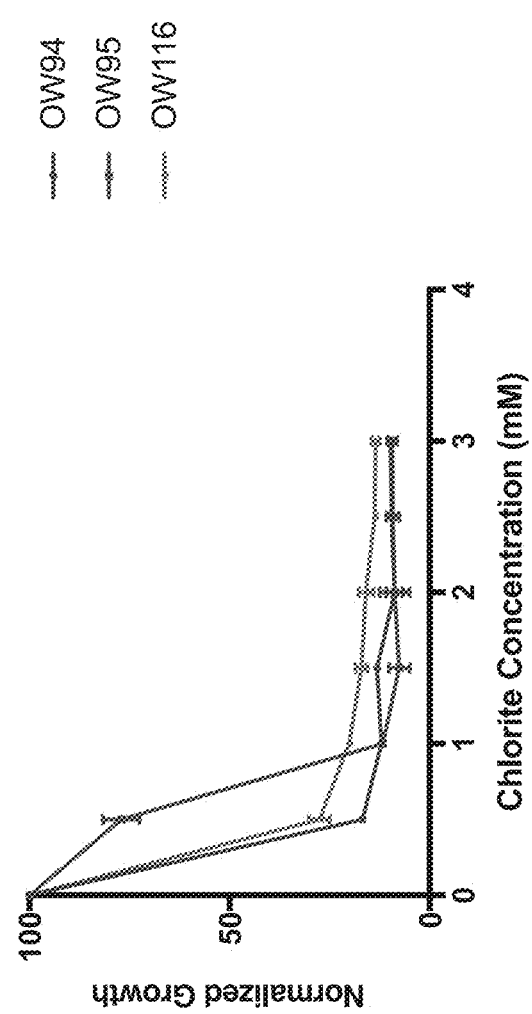

FIG. 11. Chlorite dose-response curves under anaerobic nitrate reducing conditions of different strains. OW94, RFP expressing *E. coli*, OW95 wtCld expressing *E. coli*, OW116 cCld expressing *E. coli*.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or. The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Example: Chlorite Dismutase and Chlorite Mediated Continuous Biomanufacturing Hygiene Control In this example we report the construction of a chlorite resistant *Escherichia coli* strain by heterologous expression of Cld, followed by directed evolution. Initially, chlorite half maximal inhibitory concentration ($IC_{50}$) was approximately three times higher in Cld-expressing *E. coli* than the RFP-expressing and wild type *E. coli* negative controls. Through directed evolution, we identified an A21D mutation at the Cld translocation signal peptide that enhanced chlorite resistance and subsequently discovered that cytoplasmic expression of Cld (cCld) could lead to chlorite hyper-resistance, with a chlorite $IC_{50}$ approximately 16 times higher than the negative controls. We then demonstrated that chlorite causes complete growth arrest and elicited strong stress-response in RFP-expressing *E. coli*, but not in cCld-expressing *E. coli*. Finally, we confirmed that the cCld expressing *E. coli* is compatible with continuous-flow bioreactors that contain chlorite as a biocide for contamination prevention and treatment.

Materials and Methods

Bacterial Strains, Cultivation, and Plasmid Construction

*Escherichia coli* LMG194 (wt *E. coli*) was used for optimal protein induction and for its compatibility with the pBAD arabinose promoter [212]. All *E. coli* strains were grown in a modified version of RM medium (MRM medium), described in the pBAD TOPO® TA Expression Kit user manual, with a reduced amount of casamino acids (5 g/L) and appropriate antibiotics (kanamycin 50 µg/ml or spectinomycin 100 µg/ml). All *Caulobacter crescentus* strains are derivatives of the lab-adapted NA1000 strain and were grown in peptone yeast extract (PYE) medium at 30 C. Cultures were maintained in 15% glycerol stocks frozen at −80° C.

A derivative of vector pSB4K5 (pSC101 origin of replication, ~5 copies per cell), which lacks ccdB and the pUC19 origin of replication but contains araC with the arabinose-inducible promoter [34], was used as the backbone to express *Shewanella algae* strain ACDC Cld (wtCld) (pICC63) and RFP (pICC49). The pICC63 and pICC49 plasmids were constructed by Clarks et al. for a previous study [34]. The cytoplasmic Cld (cCld) expressing plasmid, pOW61, was constructed by removing the translocation signal peptide (2-31 amino acids) of wtCld in pICC63 via "round-the-horn" site-directed mutagenesis (developed by Sean Moore, openwetware.org). The signal peptide was predicted with SignalP 4.1 Server [213]. All other plasmids are constructed via Gibson cloning with In-Fusion® HD Cloning Kit (Clontech) following the manufacture's instruction. The plasmid pTMH173 that expresses FMO (flavin-containing monooxygenase from *Methylophaga aminisulfidivorans* MP) was constructed using Golden Gate Assembly. The FMO gene is flanked by the BioBricks promoter BBa_J23100 [214] and the terminator tSPY [215]. Constructed plasmid sequences were verified at the UC Berkeley DNA sequencing facility by Sanger sequencing.

Phage Isolation and Plaque Assay

Influent wastewater samples were collected from the East Bay Municipal Utility District's wastewater treatment plant in Oakland, CA, and filtered through 0.22 µM filters to remove debris and microbes. To make a phage enrichment culture, 5 mL of filtered wastewater was mixed with 5 mL of 2× LB medium and inoculated with 100 µL of stationary *E. coli* cells, incubated for 48 hours at 37° C., 50 RPM. Next, a sterile cotton swab was dipped into an overnight *E. coli* culture, smeared on an LB agar plate, and 10 µL of the phage enrichment culture was then spotted on the plate. The plate was incubated overnight at 37° C. Positive lytic phage activity resulted in a clear zone on the *E. coli* lawn. Phage particles from the clear zone were picked into the phage buffer (10 mM Tris, 1 mM CaCl2 10 mM MgCl2, 68 mM NaCl, pH 7.5, adapted from the Phage Hunting Program, University of Pittsburgh), followed by dilution to extinction and plating to obtain single plaques with pure phage cultures. Phage cultures were maintained at 4° C. in the phage buffer. The pure phage culture was incubated with 4 mM chlorite or water at 37° C., followed by plating on LB plates at different time points to test phage inactivation by chlorite. To test phage deactivation by chlorite, *C. crescentus* phage CR-30 was incubated with chlorite or water at 30 C. Samples were taken at designated time points and mixed with PYE (0.3%) agar and log phase (OD660 0.1-04) *C. crescentus* culture before plating on PYE plates. Plaque forming unites were counted after 24 hours.

Protein Expression in *E. coli*

Heterologous expression of Cld in the *E. coli* periplasm is difficult and usually requires a low induction temperature (20° C.) and/or addition of a heme-precursor [205, 207]. Our first attempt to express Cld with the inducible pET promoter was unsuccessful and produced mostly insoluble Cld that failed to provide chlorite resistance. Addition of the heme precursor hemin (10 mM) did not affect Cld expression in any strain (data not shown). To overcome these expression problems, a low-copy number vector was used, which allows for the slow but steady expression of Cld (see plasmid construction section for details). To induce protein expression prior to experiments, *E. coli* strains were revived from freezer stocks by streaking out to single colonies on LB agar plates with the appropriate antibiotics. Single colonies from plates were picked into MRM medium and cultivated overnight at 37° C., 250 rpm. The next day, 100 µL of the overnight cultures were inoculated into 10 mL MRM medium and incubated at 37° C., 250 rpm. The incubation temperature was adjusted to 26° C. and 0.02% w/v arabinose was added to induce the protein expression when the optical density at 600 nm (OD600) reached approximately 0.4.

Protein expression was induced for 18 hours before use in downstream experiments. All *E. coli* strains were treated with an identical procedure for protein induction, with the exception FMO expressing strains, which were under a constitutively active promoter.

Half Maximal Inhibitory Concentration ($IC_{50}$) Determination

For $IC_{50}$ determination, flat-bottom 96-well plates (Corning Costar, Tewksbury, MA) were inoculated with *E. coli* strains at a starting OD600 of 0.02 in 100 µL of 2×MRM medium, with 0.02% w/v arabinose and appropriate antibiotics. 2× sodium chlorite stock solutions with various concentrations were prepared on the day of experiment, and 100 µL was added to the plate to achieve the desired chlorite concentrations. 100 µL of water was added to the negative control wells. The plate was then placed in a shaker and cultivated overnight at 37° C., 250 rpm. $IC_{50}$ were determined 24 hours after inoculation by measuring OD600. The OD600 difference between final and initial reads was normalized to the no chlorite addition negative control to determine the final normalized growth.

Chlorite Dismutase Activity Assay

Whole cells and cell lysates were used to determine the Cld activity. After induction of Cld or RFP expression, 10 mL of RFP-expressing OW94, wtCld-expressing OW95, and cCld-expressing OW116 cells were normalized to an OD600 nm of 2.0. Cells were then washed three times and resuspended in 1 mL of 100 mM potassium phosphate buffer (KPi buffer, 3.619 g/L $KH_2PO_4$ and 4.63 g/L $K_2HPO_4$). Cells in KPi buffer were then subjected to sonication (QSonica) at 4° C. to generate cell lysate. A Qsonica sonicator was used with an amplitude of 50 and a total process time of 2 minutes. The protein concentration in the cell lysate was quantified with a BCA Protein Assay Kit (Thermo Fisher Scientific) following manufacture's protocol. To determine the Cld activity in different strains, 20 µL of resuspended whole cells (normalized to an OD600 nm of 2) or cell lysate (normalized to 0.5 mg/mL) was transferred into a quartz cuvette (Fisher Scientific) containing 1 mL of KPi buffer, and a final concentration of 500 µM of chlorite was added followed by rapid mixing via pipetting. Chlorite concentration was monitored immediately after chlorite addition based on absorption at 260 nm. Sodium chlorite from Sigma-Aldrich (CAS Number 7758-19-2) was used to generate a standard curve.

Directed Evolution

OW95 cells were revived from freezer stocks, transferred into liquid MRM medium, and induced for Cld expression as described above. Initially, eight isogenic independent cultures were cultivated with a starting OD600 nm of 0.01 in MRM medium with 1 mM chlorite, 0.02% w/v arabinose, and 50 µg/mL of kanamycin, at 37° C., 250 rpm. The resulting cultures were repeatedly transferred everyday with increasing chlorite concentrations (increments of 1 mM) in the medium. Cultures were subjected to three transfers with the previous concentration of chlorite if they failed to tolerate the increased chlorite concentration. The directed evolution was concluded when we obtained a strain (OW105) that was able to grow in the presence of 8 mM chlorite and reached a similar final OD600 as without chlorite control.

Western Blot

For western blots, *E. coli* strains were harvested and normalized to an OD of 2.0, and cell lysate was generated as described in the above. Cell lysates were centrifuged, and the resulting supernatant was collected as the cell soluble fraction, whereas the membrane debris-containing pellet was resuspended in 8M urea and referred as the insoluble fraction. The insoluble fraction could also contain small amount of whole cells due to lysing inefficiency. The primary rabbit antibodies against Cld and horseradish peroxidase conjugated anti-rabbit secondary antibodies were used at a 1:5000 dilution [216] Immobilon western chemiluminescent hrp substrate (Millipore) was used following the manufacturer's protocol to reveal the blot. Purified *Azospira suillum* PS Cld (accession number: G8QM51, 96% identical to *S. algae* ACDC Cld) was used as a positive control.

Proteomic Analysis

For proteomic analysis, *E. coli* strains with or without chlorite (0.4 mM for OW94, 4 mM for OW116) were cultured and harvested at late log phase, centrifuged, resuspended, and lysed by sonication (QSonica) at 4° C. Less chlorite and a larger culture volume was used for OW94 due to poor cell yield in the presence of chlorite. Protein concentration was determined with a BCA Protein Assay Kit (Thermo Fisher Scientific) following manufacturer's protocol. A tryptic digestion procedure was used to prepare our samples for mass spectrometry [35]. Liquid chromatography coupled to tandem mass spectrometry of trypsin-digested samples was performed at the QB3 mass spectrometry facility at UC Berkeley and the resulting data were analyzed with the Progenesis software. A protein with a confidence score >100, p-value <0.05, and maximal normalized peptide abundance fold change >2 is considered differentially expressed.

Chemostat Setup and Operation Parameters

A 2 L round-bottom autoclavable laboratory fermenter (BiOENGiNEERiNG), was operated as an iso-volumetric chemostat with 1 L of MRM medium in the bioreactor vessel. Temperature, dissolved oxygen (dO), and pH were monitored during the course of the experiments. Temperature was set and maintained at 37° C. pH was set to 7.2 and adjusted automatically based on the real time pH value with 1M NaOH or 1M HCl. dO was set to 20% of the maximal dO value at 37° C. with constant air flow of 2 L/min. Constant dO was maintained by automatic agitation speed adjustment based on the real-time dO value. Agitation speed varied between 200-700 RPM, depending on oxygen demand. Two separate pumps were used to control medium inflow and waste outflow rates.

To determine the specific growth rate before and after spiking chlorite into the chemostat, after induction of Cld or RFP expression, 10 mL of OW94, or OW116 cells were inoculated into the bioreactor containing 1 L MRM medium with 0.02% w/v arabinose and 50 µg/mL of kanamycin. The chemostat at first operated as a batch culture (dilution rate equal to 0), until the culture reached mid-log phase (OD600 of ~0.7-1.0), then dilution rate was set to be approximately equal to the cell growth rate. This allowed the bioreactor to achieve a zero net growth while maintaining a near-maximum specific growth rate. 4 mM of chlorite was spiked into the chemostat 1 hour later, and the dilution rate was adjusted in an attempt to reestablish the equilibrium state. The specific growth rate before chlorite spike was determined based on the batch mode growth, whereas specific growth rate after the chlorite spike was calculated as the dilution rate plus actual growth or wash out rate [217]. All growth data were plotted and calculated using the Prism 7 software. The batch growth kinetics of stationary cells were tested in 96-well plate under different chlorite concentrations in MRM medium at 37° C., with shaking, on a Tecan Sunrise microplate readers.

To test the effectiveness of chlorite as a biocide in the chemostat, after induction of Cld and RFP expression, 10 mL of RFP and cCld expressing *E. coli* strain OW115 cells were inoculated into the bioreactor containing 1 L MRM medium with 0.02% w/v arabinose. We deliberately contaminated our reactor with 10 mL of creek water from Strawberry Creek (Berkeley, CA), which is heavily contaminated by coliforms such as *E. coli* [218]. The dilution rate was increased from 0 to 0.3/hr after the inoculated culture reached mid-log phase. After the reactor was deemed contaminated (when the culture changed color from pink to milky white), 8 mM chlorite was spiked into both the reactor and medium reservoir. The negative control run did not receive the chlorite spike treatment. Culture samples were taken from the reactor twice a day, diluted 100 times in sterile MRM medium, and counted in a Guava® easyCyte flow cytometer. Total and RFP-positive cells from 15 μL of each sample were counted based on red fluorescent signal. Flow-cytometry data were visualized and analyzed via the cloud-based Cytobank tool [219].

To test how chlorite affects bio-indigo production, 10 mL of Fmo and cCld expressing *E. coli* strain OW117 overnight culture was inoculated into the chemostat containing 1 L of MRM medium and 4 mM chlorite, with 1 g/L of tryptophan added to the medium to enhance bio-indigo yield. The negative control did not receive chlorite. The dilution rate was adjusted from 0 to 0.08/hr after the inoculated culture reached late-log phase. After indigo production yield stabilized (after 30 hours), 10 mL of the Strawberry Creek water enrichment culture at OD ~2.0 was added into the bioreactor. To make the Strawberry Creek water enrichment culture, 1 mL of Strawberry Creek water was mixed with 9 mL of MRM medium, at 37° C., 250 rpm, overnight. Chlorite concentration was monitored and re-adjusted to 4 mM. Samples were taken from the reactor twice a day to determine the bio-indigo yield.

Bio-Indigo Extraction and Measurement

Indigo is poorly soluble in water thus was extracted from bioreactor samples using dimethyl sulfoxide (DMSO). 180 μL of DMSO was added to 20 μL of culture, mixed by vortexing, and centrifuged at 13,000 rcf for 10 minutes to remove cells debris. The supernatant containing soluble indigo was transferred to a 96-well plate, and the concentration of indigo was determined based on absorption at 650 nm. Indigo purchased from Sigma-Aldrich (CAS Number 482-89-3) was used to generate a standard curve.

Results

Cld Expressing *E. coli* Results in Chlorite Resistance

Figure 1A:
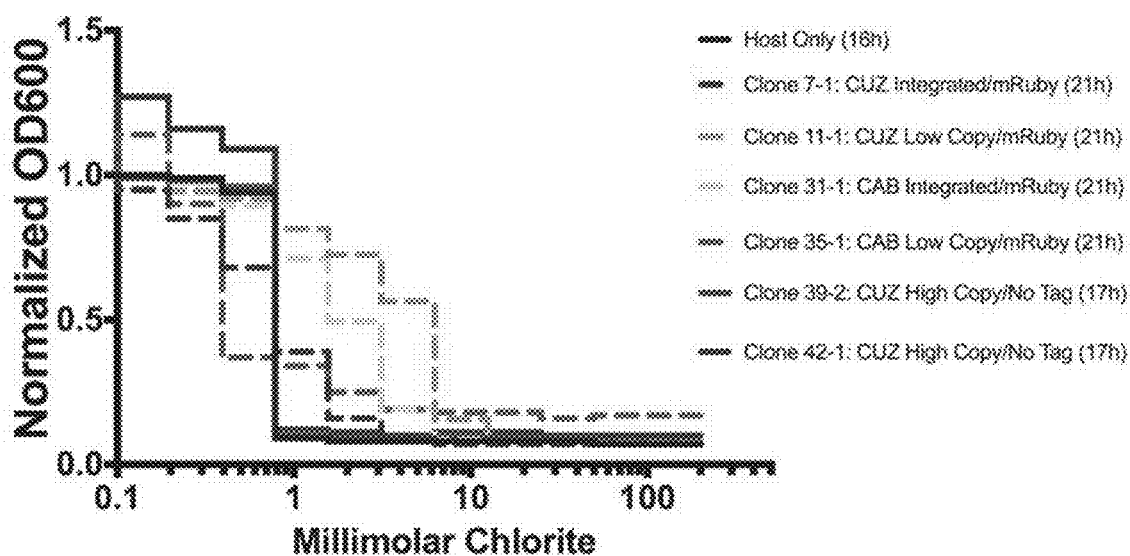
Figure 1B:
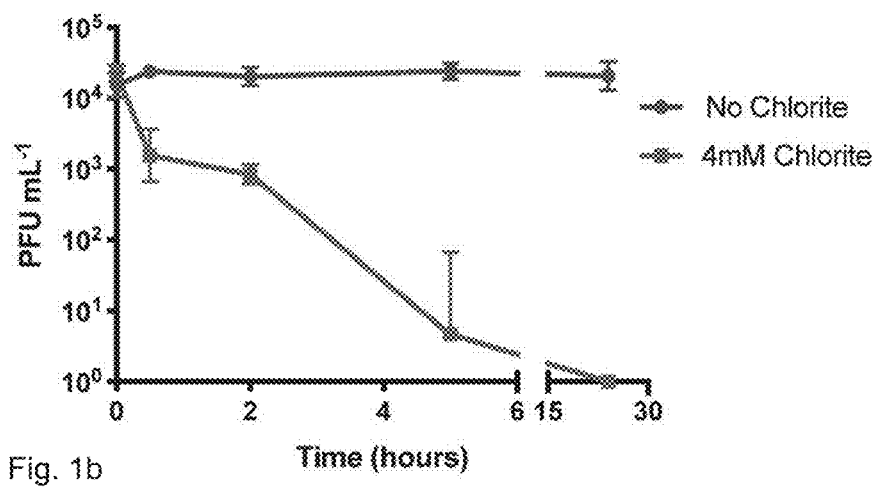
Figure 1C:
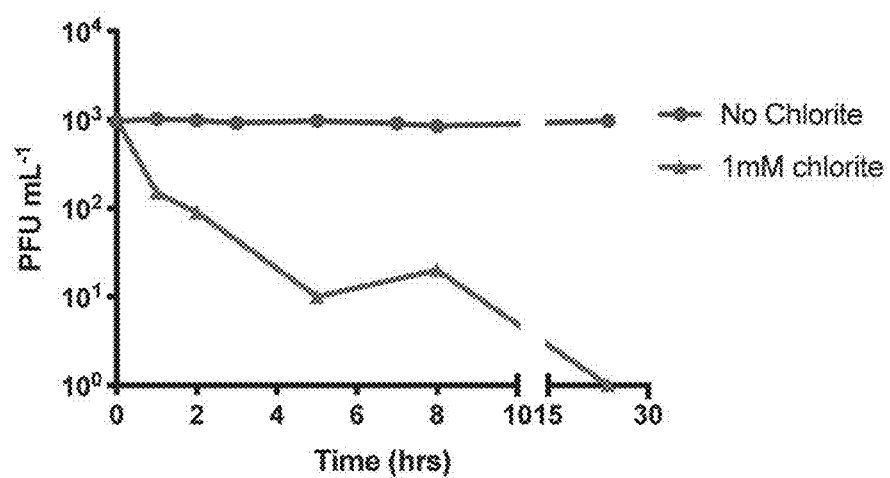

During our study of perchlorate reducing bacteria, we have observed that the naturally perchlorate-reducing bacterium *Azospira suillum* PS grew aerobically in the presence of 40 μM chlorite, while the cld deletion (Acid) mutant failed to grow (unpublished observations). Additionally, heterologous Cld expression protected against chlorite toxicity in aerobic *Shewanella oneidensis* MR-1 (unpublished observations) and *Caulobacter crescentus* culture (unpublished observations), and *Saccharomyces cerevisiae* (FIG. 1*a*). These data suggested that Cld plays an important role in chlorite resistance under aerobic conditions. We also tested and observed chlorite-induced phage inactivation in *C. crescentus* and *E. coli* lytic phages similar to a previous study (FIG. 1 *b,c*) [28]. These results imply that chlorite-induced phage inactivation could be a general phenomenon. These preliminary results also indicate that chlorite could be a superior treatment than traditional antibiotics in terms of activity spectrum, potency, and process economics. This inspired us to pursue a biocide/biocide resistance system based on chlorite and Cld.

Figure 2A:
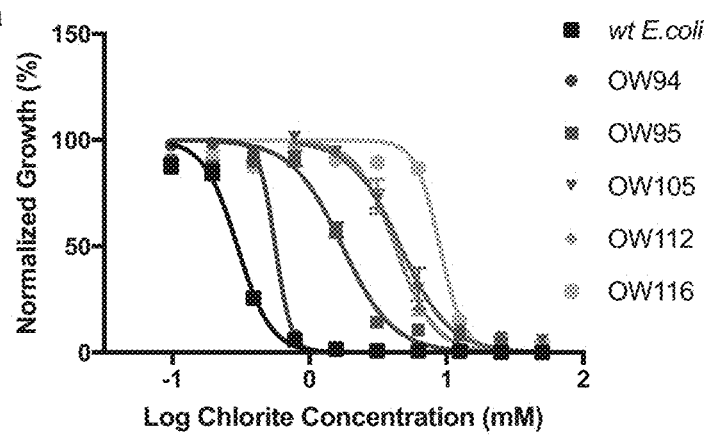
Figure 2B:
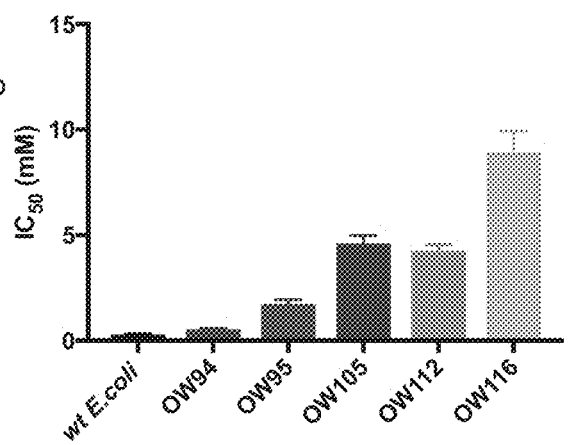

In order to obtain a chlorite resistant microbial host with industrial applications, the wtCld from a chlorate reducer, *Shewanella algae* ACDC, was heterologously expressed in *E. coli* strain LMG194. The resulting strain, wtCld-expressing OW95 showed a three-fold increase in chlorite resistance ($IC_{50}$=1.74 mM, 95% confidence interval [CI] 1.56 to 1.94 mM) compared to our negative controls RFP-expressing *E. coli*, OW94 ($IC_{50}$=0.56 mM, 95% CI=0.55-0.58 mM), and the parental LMG194 ($IC_{50}$=0.30 mM 95% CI=0.28-0.31 mM) (FIG. 2 *a,b*). The RFP negative control was used to account for non-specific protein reactivity toward chlorite. Interestingly, enhanced chlorite resistance was observed in OW95 if Cld expression was induced at 26° C., but not at 37° C. However, after induction at 26° C., OW95 cultures displayed enhanced chlorite resistance when tested at 37° C., indicating the wtCld was functional at 37° C. but failed to express or fold properly.

Figure 3:
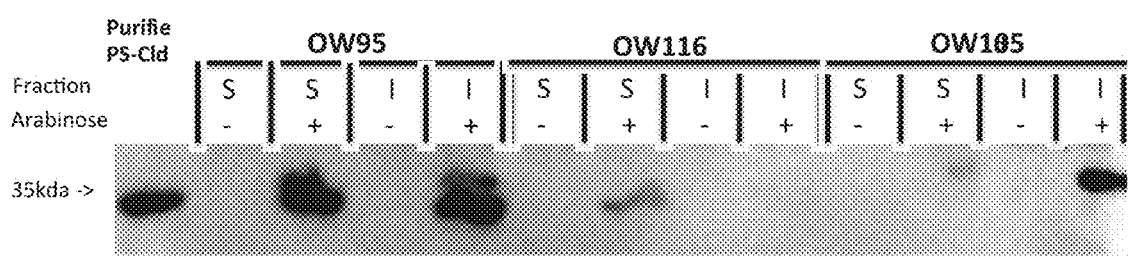

To further enhance chlorite resistance, we conducted a directed evolution experiment with OW95 by repeatedly subculturing (with overnight cultures) the strain into increasing concentrations of chlorite at 37° C. At the end of the directed evolution experiment, we obtained a chlorite hyper-resistant strain OW105 ($IC_{50}$=4.60 mM, 95% CI=4.26 to 4.98 mM) (FIG. 2 *a,b*), and identified the causative mutation as an alanine to aspartate (A21D) mutation in the translocation signal peptide of Cld (see method for more detail). Such mutation likely inhibited signal peptide processing and/or translocation through the inner membrane. To test this hypothesis, western blot analysis was conducted with OW95, OW105, and a cCld (translocation signal peptide removed) expressing strain OW116 to determine the consequences of A21D mutation (FIG. 3, 4). As a periplasmic enzyme, unprocessed (with its signal peptide) Cld is predicted to translocate through the inner membrane via the Sec pathway [220], followed by peptidase cleavage of the signal peptide to produce the mature Cld with a slight decrease in molecular weight. In the western blot, bands indicating processed mature Cld at ~35 kDa could be seen in the purified Cld positive control, both soluble and insoluble fractions of OW95, and the soluble fraction of OW116, but was absent in OW105, and samples without arabinose induction. The mature Cld band in OW116 was significantly fainter than ones in OW95, which implies potential Cld copy number control in the cytoplasm. As expect, when induced with arabinose, a band corresponding to the unprocessed Cld was present in the OW95 insoluble fraction, but not in OW116, as cytoplasmic Cld does not go through peptidase processing. Interestingly, mature Cld was absent but one band that likely corresponds to unprocessed Cld was present in the insoluble fraction of OW105. Taken together, these results suggest that the A21D mutation in OW105-Cld resulted in loss of localization and/or signal peptide processing capability. Based on this observation, we predicted the cCld could potentially enhance chlorite tolerance. Strikingly, OW116 showed the highest chlorite resistance ($IC_{50}$=8.94 mM, 95% CI=8.07 to 9.93 mM) (FIG. 2 *a,b*) among different Cld-expressing strains, demonstrating that expression of cCld is more advantageous than the A21D mutant Cld or wtCld.

One explanation of the enhanced chlorite resistance in cCld expressing OW116 is through heightened chlorite decomposition activity, which is undesirable, as it would cause rapid chlorite degradation and loss of medium selectivity. Therefore, to compare Cld activity among different strains, we measured the chlorite dismutase activity of whole cells and cell lysates of OW94, OW95 and OW116 (FIG. 5 *a-d*). As expected, OW94 did not react with chlorite, whereas OW95 demonstrated rapid Cld activity in both whole cells and cell lysate. Unexpectedly we did not detect significant Cld activity in OW116 whole cells and only observed low, though significant, Cld activity in OW116 cell lysate, indicating membrane impermeability limiting the influx of chlorite into the cytoplasm. The Cld activity in OW95 and OW116 cell lysates were much lower than published Cld activity in (per)chlorate reducer cell lysates [221-223], which ranged from 130 to 1928 umol of chlorite $mg^{-1}$ $minute^{-1}$. These results suggested that the increased chlorite resistance in OW116 was not due to heightened Cld activity, but other unknown mechanisms involving the enzyme's cellular localization.

Exposure to Chlorite Causes Growth Arrest and Oxidative Stress, but these Effects are Greatly Diminished in the cCld-Expressing OW116

While our previous chlorite $IC_{50}$ experiment determines the chlorite resistance based on cell yield, it does not account for changes of the specific growth rate. During continuous bioprocessing, the bioreactor dilution (production) rate could be restricted by the specific growth rate of the processing organism; a slow-growing strain is unwanted and could potentially hamper overall volumetric yield. To understand the impact of chlorite on the specific growth rate of batch cultures, we assayed the growth kinetics of OW94 and OW116 under different chlorite concentrations (FIG. 6 a-d). As chlorite concentration increased, the specific growth rate of OW94 drastically decreased (FIG. 6a, c), but only reduced slightly in OW116 (FIG. 6b, d). To investigate if a similar result can be seen in actively growing cultures, we spiked 4 mM chlorite into bioreactors with growing OW94 or OW116 during the equilibrium growth state (FIG. 6c, d, FIG. 7 a-g). During equilibrium growth, the dilution rate is roughly equal to the maximum specific growth rate, resulting in a zero net growth while the cells are growing at near maximum growth rate. Before the chlorite spike, OW94 and OW116 were growing with a specific growth rate of 0.88±0.39 and 0.87±0.13 $hr^{-1}$, respectively. After the chlorite spike, OW94 never reached a new equilibrium growth state and washed out overtime despite our attempts to reestablish its equilibrium growth state by changing the dilution rate. Its specific growth rate also dropped to near or below zero (0.01±0.07 $hr^{-1}$) after the spike, indicating complete growth arrest and/or cell lyses. As expected, OW116 was still able to grow after the chlorite spike due to the protective effect of cCld; however, the specific growth rate of OW116 was reduced by ~20% to 0.64±0.10 $hr^{-1}$.

Figure 8:
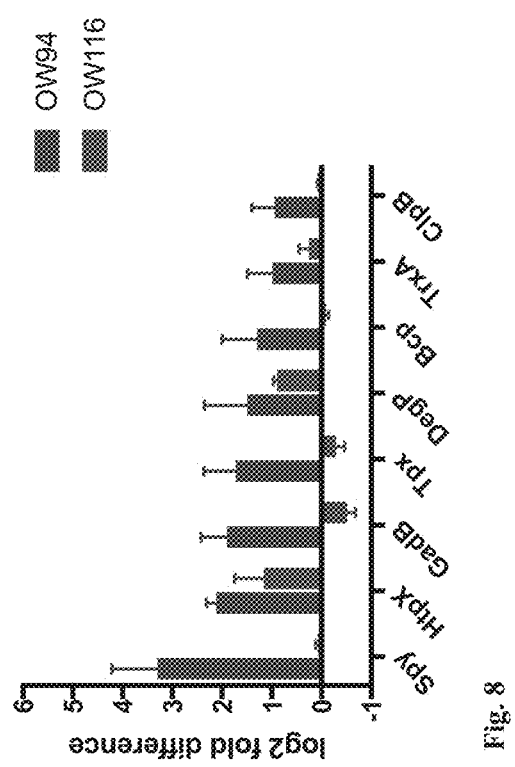

To further investigate why the growth rate of OW116 was reduced and to gain insight for possible future strain improvement, we conducted proteomic experiments to compare the stress-induced protein expression profiles of OW94 and OW116, with and without chlorite. A total 52 proteins from the chlorite sensitive strain OW94 and 11 proteins from the chlorite resistant strain OW116 displayed peptide abundance changes greater than 2-fold in response to chlorite addition. Eight stress response proteins were induced in OW94 (FIG. 8): stress-induced chaperone Spy (Accession: P77754) and ClpB (Accession: P63284); periplasmic and membrane proteases DegP (Accession: P0C0V0) and HtpX (Accession: P23894); oxidative stress and redox homeostasis proteins Tpx (Accession: P0A862), Bcp (Accession: P0AE52), and TrxA (Accession: P0AA25); and acid stress protein GadB (Accession: P69910). These findings indicted that OW94 was experiencing chlorite-induced oxidative stress, which led to protein denaturation, misfolding and degradation, as well as a disturbed redox environment. In OW116 only the proteases DegP and HtpX were similarly induced, whereas other stress proteins up-regulated in OW94 remained mostly unchanged (FIG. 8), implying a much milder effect of chlorite-induced oxidative stress.

Figure 9A:
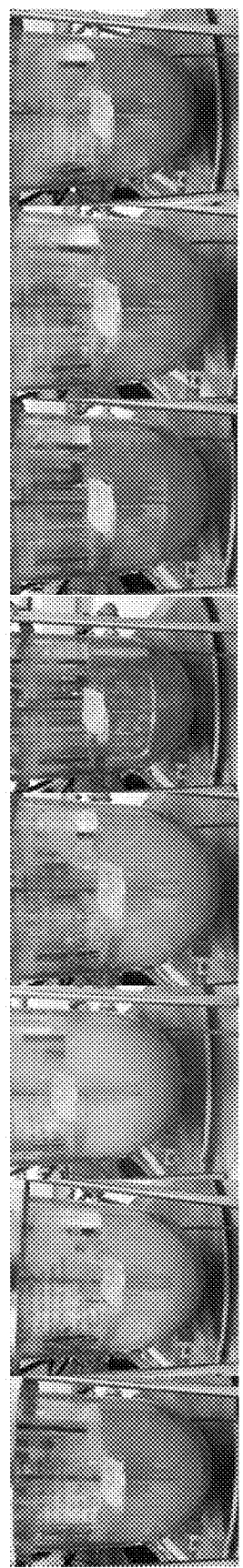
Figure 9B:
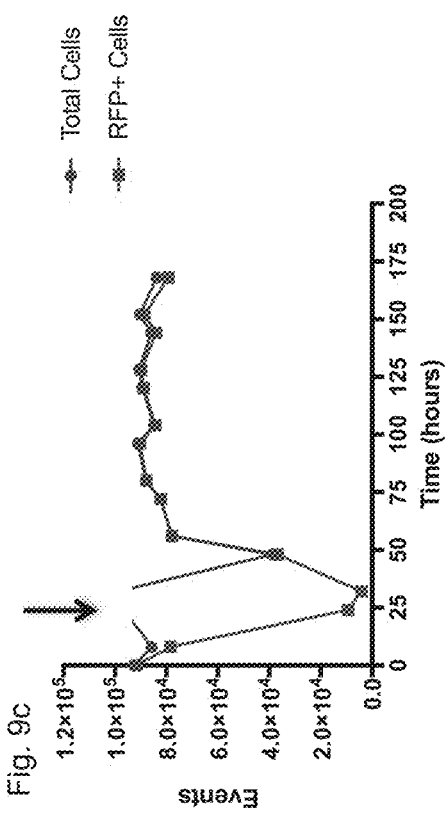
Figure 9D:
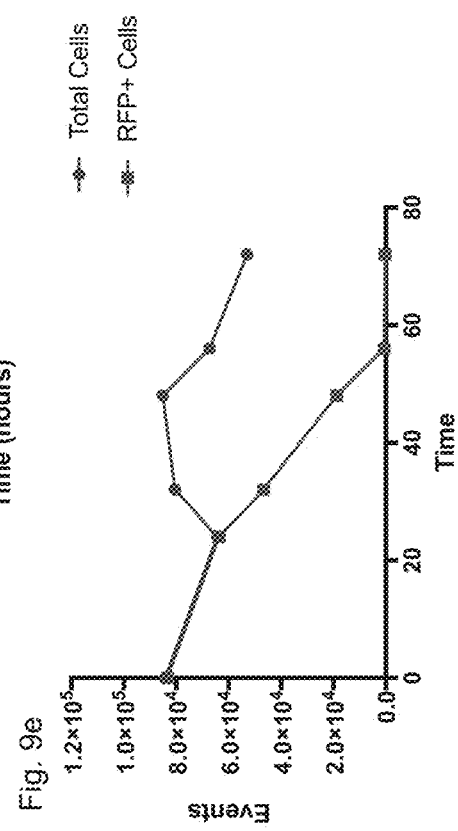
Figure 9C:
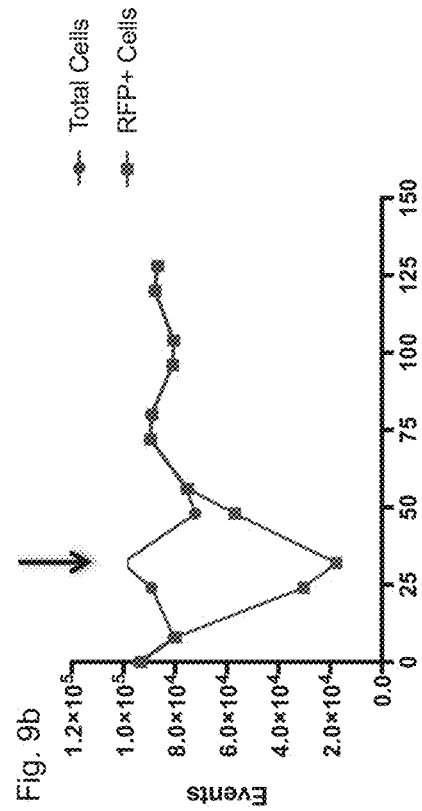
Figure 9E:
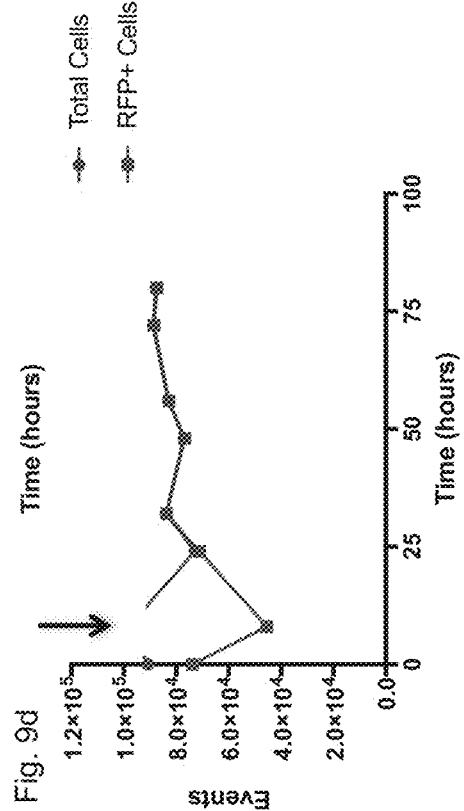

Chlorite/Cld can be Used as a Biocide/Biocide-Resistance System for Treatment or Prevention of Contamination in a Continuous Flow Bioreactor We also sought to demonstrate that chlorite in combination with Cld can be applied as a biocide/biocide resistant system to treat and prevent bioreactor contamination. To examine if addition of chlorite could rescue a contaminated bioreactor, we deliberately contaminated our reactor with 1% (v/v) raw environmental water sample from a site that is known to be heavily contaminated by coliforms [218], and subsequently treated it with 10 mM chlorite. An E. coli strain expressing both cCld and RFP (OW115) that mimics an industrial protein production strain was used to inoculate bioreactors. Flow cytometry was performed to track RFP positive (RFP+) cells vs. total cells in the bioreactors. In the absence of chlorite, the RFP+OW115 cells were slowly outcompeted by contaminants, as evidenced by the change in color of the cultures from red/pink to milky white (FIG. 9a). Strikingly, after 10 mM chlorite was spiked into the reactor, the culture returned to its original pink color as the contaminants were inhibited and washed out from the reactors. Flow cytometry showed a steady decline of the RFP+ population before the chlorite spike (FIG. 9 a-d), followed by RFP+ cells recovery and reestablishment as the dominant population after the spike, consistent with our visual observation (FIG. 9 a-d). In control cultures without chlorite addition, RFP-expressing cells continuously declined without recovery (FIG. 6e). Our data thus indicate that chlorite can be used as a biocide to effectively eliminate contaminants in a continuous-flow bioreactor.

To demonstrate that chlorite can also protect a commodity bioprocessing strain from contamination, we constructed an E. coli strain (OW117) that constitutively expressed cCld and the indigo-producing, flavin-containing monooxygenase (FMO) from Methylophaga aminisulfidivorans MP [224, 225]; and a control E. coli strain (OW118) that constitutively expresses only FMO. An enriched microbial community (SCW enrichment) from Strawberry Creek was used to mimic environmental contaminants. We switched from the pBAD promoter to a constitutively active promoter due to an unknown compatibility problem of FMO with Cld and pBAD promoter. In batch growth without chlorite, SCW enrichment culture showed faster growth kinetics than both OW117 and OW118 (FIG. 10a); however, only OW118 could endure medium with chlorite due to the presence of cCld (FIG. 10b, c). Unlike the robust chlorite resistance seen in OW116, chlorite addition resulted in a more severe defective growth phenotype in OW118, indicating that expression of flavin-containing protein likely exacerbated the chlorite-induced stress. To test whether the chlorite/Cld system also protects OW117 against SCW enrichment in a continuous flow system, we inoculated bioreactors with OW117 with and without the addition of 4 mM chlorite (FIG. 10d). After two days of bio-indigo production, 10 mL of the SCW enrichment culture with an OD of ~2.0 was added to the bioreactors. As expected, indigo yields plummeted after the addition of contaminants in the absence of chlorite, presumably because OW117 failed to compete with the environmental microbes. However, in the presence of chlorite, indigo was steadily produced until the end of the experiment, indicating that chlorite addition can successfully prevent contamination of a continuous flow bioreactor.

DISCUSSION

Contamination remains a major challenge in continuous bioprocessing as the processing strain can be easily outcompeted by microbial contaminants. Antibiotic use in continuous-flow bioreactor is undesirable due to its high cost. In contrast, the chlorite/Cld system offers a cheap, effective, and environmentally friendly alternative for bioreactor hygiene control and maintenance.

Heterologous expression of Cld in *E. coli* has been previously shown in many studies on the biochemical properties and enzymatic mechanisms of Cld, which have used purified Cld from *E. coli* [201, 204-211]. Nevertheless, this study is the first to demonstrate that Cld-expressing *E. coli* can tolerate high concentrations of chlorite. Expression of wtCld has been problematic; likely due to protein misfolding and/or co-factor limitation combined with sudden bursts of protein expression upon induction with a strong promoter such as the T7 promoter used in pET expression vectors. By using a lower copy vector and inducing at a relatively low temperature, we were able to functionally express wtCld that was correctly processed and translocated to the periplasm (as evidenced by shifted protein size).

We have demonstrated that cytoplasmic expression of *S. algae* strain ACDC Cld in *E. coli* can prevent and treat microbial contamination during continuous bioprocessing. The high chlorite resistance and low chlorite dismutase activity observed in cCld-expressing cells is ideal for maintaining a stable population of the desired strain in chlorite-containing bioreactors. We recommend a concentration of 4 mM chlorite for *E. coli* continuous-flow bioreactors for maximal contaminant inhibition without adverse effects. This work establishes the use of chlorite and Cld as an alternative method for robust continuous bioprocessing and bioreactor hygiene control, to transition from batch and fed-batch reactors to continuous-flow bioreactor in the biotech industry, and can significantly enhance the bioprocessing economics.

REFERENCES

18. Youngblut M D, et al. *Annual Review of Microbiology* 2016, 70:435-457.
19. Coates J D, et al. *Nature Reviews Microbiology* 2004, 2(7):569-580.
20. Condie L W: *J (American Water Works Association)* 1986:73-78.
21. Daniel F B, *Journal (American Water Works Association)* 1990, 82(10):61-69.
22. Vanwijk D J, *Ecotoxicology and Environmental Safety* 1995, 32(3):244-253.
23. Ingram P R, *Archives of Biochemistry and Biophysics* 2003, 410(1):121-133.
24. Ingram P R, *Free radical research* 2004, 38(7):739-750.
25. Gagnon G, et al. *Water Research* 2005, 39(9):1809-1817.
26. van Wijk et al. *Ecotoxicology and environmental safety* 1998, 40(3):206-211.
27. Allende A, *Food Control* 2009, 20(3):230-234.
28. Bichai F, *Water quality research journal of Canada* 2006, 41(4):375-382.
29. Luo Y, *LWT—Food Science and Technology* 2011, 44(7):1621-1625.
30. Dempster R P., *The Progressive Fish-Culturist* 1988, 50(1):51-55.
31. Åslander A: Experiments on the Eradication of Canada Thistle: *Cirsium arvense*, with Chlorates and Other Herbicides: US Government Printing Office; 1928.
32. Youngblut M D, *Journal of Biological Chemistry* 2016.
33. Clark I C, *Mbio* 2013, 4(4):e00379-00313.
34. Clark I C, *Molecular microbiology* 2014, 94(1):107-125.
35. Clark I C, *MBio* 2015, 6(3):e00282-00215.
148. Melnyk R A, *BMC genomics* 2015, 16(1):862.
149. Melnyk R A, *mBio* 2014, 5(1):e00769-00713.
197. van Ginkel C G, *Archives of microbiology* 1996, 166(5):321-326.
198. Hofbauer S, *Biotechnology journal* 2014, 9(4):461-473.
199. Schaffner I, *Archives of biochemistry and biophysics* 2015, 574:18-26.
200. Lee A Q, *PNAS* 2008, 105(41):15654-15659.
201. Streit B R, *Journal of the American Chemical Society* 2010, 132(16):5711-5724.
202. DuBois J L, In: *Sustaining Life on Planet Earth: Metalloenzymes Mastering Dioxygen and Other Chewy Gases*. Springer; 2015: 45-87.
203. Clark I C, *Environmental microbiology* 2016.
204. de Geus D C, *Journal of molecular biology* 2009, 387(1):192-206.
205. Thorell H D, *Biochimica et Biophysica Acta* 2002, 1577(3):445-451.
206. Danielsson Thorell H, *European J biochemistry* 2004, 271(17):3539-3546.
207. Streit B R, *Biochemistry* 2008, 47(19):5271-5280.
208. Maixner F, *Environmental microbiology* 2008, 10(11):3043-3056.
209. Kostan J, *Journal of structural biology* 2010, 172(3):331-342.
210. Hofbauer S, *Biochemistry* 2012, 51(47):9501-9512.
211. Mlynek G, *Journal of bacteriology* 2011, 193(10):2408-2417.
212. Guzman L M, *J Bacteriol* 1995, 177(14):4121-4130.
213. Petersen *Nature methods* 2011, 8(10):785-786.
214. Anderson J, *Journal of Biological Engineering* 2010, 4(1):1.
215. Chen Y-J, *Nature Methods* 2013, 10:659.
216. O'Connor S M, *Applied and environmental microbiology* 2002, 68(6):3108-3113.
217. Jannasch H W: *Journal of Bacteriology* 1969, 99(1):156-160.
218. Hans K, Maranzana S: Strawberry Creek Water Quality—2006 Status Report. *University of California, Berkeley Office of Environment, Health & Safety (EH&S)* 2006.
219. Kotecha N, *Current protocols in cytometry* 2010:10.17. 11-10.17. 24.
220. Bagos P G, *Bioinformatics* 2010, 26(22):2811-2817.
221. Lindqvist M H, *Applied and environmental microbiol* 2012, 78(12):4380-4385.
222. Van Ginkel C, *Archives of microbiology* 1996, 166(5):321-326.
223. Coates J D, *Applied and Environmental Microbiology* 1999, 65(12):5234-5241.
224. Chen Y, *PNAS* 2011, 108(43):17791-17796.
225. Choi H S, *Biochemical and biophysical research comm* 2003, 306(4):930-936.

The invention claimed is:

1. A method for microbial contamination control in bioprocessing or improving industrial fermentation hygiene, the method comprising operating a bioreactor comprising a cultured cell expressing a cytoplasmic chlorite dismutase (cCld) sufficient to increase chlorite resistance of the cell, and chlorite sufficient to substantially inhibit growth of one or more contaminating microorganisms in the bioreactor yet permissive to, and not substantially inhibitory of, growth of the cell, wherein the cCld is engineered from a wild-type to lack a functional N-terminal translocation peptide, which results in an inability of the cell to translocate the cCld from the cell cytoplasm into the periplasm, with chlorite sufficient to substantially inhibit growth of the one or more contaminating microorganisms in the bioreactor yet not substantially inhibit growth of the cell, to achieve microbial contamination control in bioprocessing or improving industrial fermentation hygiene, wherein the cCld comprises a mutation that inhibits signal peptide processing or translocation through the inner membrane, comprising one or more point or deletion mutations within residues 2-31 of the cCld, that is a point mutation that is alanine to aspartate at residue 21 of the cCld (A21D).

2. The method of claim 1, wherein the cCld is heterologous to the cell, derived from a different species cell.

3. The method of claim 1, wherein the cell does not naturally express a chlorite dismutase.

4. The method of claim 1, wherein the cell is a bacterial, yeast, or fungal cell selected from: *Saccharomyces* sp., *Saccharomyces cerevisiae*, *Saccharomyces monacensis*, *Saccharomyces bayanus*, *Saccharomyces pastorianus*, *Saccharomyces carlsbergensis*, *Saccharomyces pombe*, *Trichoderma reesei*, *Neurospora crassa*, *Neurospora* sp., *Kluyveromyces* sp., *Kluyveromyces marxiamus*, *Kluyveromyces lactis*, *Kluyveromyces fragilis*, *Pichia stipitis*, *Pichia pastoris*, *Pichia* sp., *Sporotrichum thermophile*, *Candida shehatae*, *Candida tropicalis*, *Neurospora crassa*, *Zymomonas mobilis*, *Clostridium* sp., *Clostridium saccharoperbutylacetonicum*, *Clostridium phytofermentans*, *Clostridium thermocellum*, *Clostridium beijerinckii*, *Clostridium acetobutylicum*, *Clostridium botulinum*, *Clostridium butyricum*, *Clostridium diolis*, *Clostridium ljungdahlii*, *Clostridium aerotolerans*, *Clostridium cellulolyticum*, *Clostridium tyrobutyricum*, *Clostridium pasteurianum*, *Moorella thermoacetica*, *Escherichia coli*, *Klebsiella oxytoca*, *Thermoanaerobacterium saccharolyticum*, *Yarrowia lipolytica*, *Yarrowia* sp., *Aspergillus* sp., *Fusarium venenatum*, *Fusarium oxysporum*, *Bacillus subtilis*, and *Bacillus* sp.

5. The method of claim 1, wherein the one or more contaminating microorganisms are bacteria selected from the group consisting of *Lactobacillus*, *Clostridium*, *Pediococcus*, *Enterococcus*, *Acetobacter*, and *Gluconobacter*.

6. The method of claim 1, where the cultured cell produces an industrial fermentation product.

7. The method of claim 1, wherein the bioreactor is configured as a continuous flow bioreactor.

8. The method of claim 1, further comprising detecting a resultant inhibition of growth of the one or more contaminating microorganisms.

9. The method of claim 1, where the cultured cell produces an industrial fermentation product, and the method further comprises detecting a resultant production of the fermentation product.

* * * * *